US009687579B2

(12) United States Patent
Lindner et al.

(10) Patent No.: US 9,687,579 B2
(45) Date of Patent: Jun. 27, 2017

(54) COATED SUPERABSORBENT POLYMER PARTICLES AND PROCESSES THEREFORE

(71) Applicant: The Procter & Gamble Company, Cincinnati, OH (US)

(72) Inventors: Torsten Lindner, Kronberg (DE); Axel Meyer, Frankfurt am Main (DE); Mattias Schmidt, Idstein (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/571,319

(22) Filed: Dec. 16, 2014

(65) Prior Publication Data
US 2015/0097142 A1 Apr. 9, 2015

Related U.S. Application Data

(63) Continuation of application No. 12/838,875, filed on Jul. 19, 2010, now Pat. No. 8,945,419.

(30) Foreign Application Priority Data

Jul. 20, 2009 (EP) .................................. 09165869

(51) Int. Cl.
| *B01J 20/26* | (2006.01) |
| *B01J 13/02* | (2006.01) |
| *A61L 15/60* | (2006.01) |
| *A61L 15/22* | (2006.01) |
| *C08F 8/00* | (2006.01) |

(52) U.S. Cl.
CPC ............ *A61L 15/225* (2013.01); *A61L 15/60* (2013.01); *C08F 8/00* (2013.01)

(58) Field of Classification Search
None
See application file for complete search history.

(56) References Cited

U.S. PATENT DOCUMENTS

| 6,391,451 | B1 | 5/2002 | Mitchell et al. | |
|---|---|---|---|---|
| 7,049,000 | B2 | 5/2006 | Fossum et al. | |
| 7,270,881 | B2 | 9/2007 | Schmidt et al. | |
| 2001/0049413 | A1 | 12/2001 | Haraguchi | |
| 2005/0090586 | A1* | 4/2005 | Kang | A61L 15/60 524/27 |
| 2005/0214541 | A1 | 9/2005 | Berrada et al. | |
| 2005/0245393 | A1* | 11/2005 | Herfert | A61L 15/60 502/402 |
| 2007/0049689 | A1 | 3/2007 | Meyer et al. | |
| 2009/0018047 | A1* | 1/2009 | Mundschau | A47K 7/03 510/438 |
| 2010/0329590 | A1* | 12/2010 | Minkler | B65D 33/1691 383/6 |

OTHER PUBLICATIONS

PCT International Search Report, PCT/2010/041950 date of mailing Jul. 9, 2010.

* cited by examiner

*Primary Examiner* — Jeffrey Washville
(74) *Attorney, Agent, or Firm* — Kathleen Y. Carter

(57) ABSTRACT

Superabsorbent material, comprising first superabsorbent polymers, coated with second clay-crosslinked superabsorbent polymers, said second clay-crosslinked superabsorbent polymers being obtainable by the step of polymerization of a solution/dispersion of polymerizable compounds and clay particles, to obtain said second superabsorbent polymers, crosslinked by said clay particles, of a weight average largest particle dimension of less than 800 nm.

20 Claims, No Drawings

COATED SUPERABSORBENT POLYMER PARTICLES AND PROCESSES THEREFORE

FIELD OF THE INVENTION

The present invention relates to superabsorbent material, and processes for making this and articles containing it, comprising first superabsorbent polymers, coated with second clay-crosslinked superabsorbent polymers, said second clay-crosslinked superabsorbent polymers being obtainable by the step of polymerization of a solution or dispersion of polymerizable compounds, in the presence of a nano-sized clay particle dispersion, to obtain said second superabsorbent polymers, crosslinked by said clay particles, said clay particles having a weight average largest particle dimension of less than 800 nm.

BACKGROUND TO THE INVENTION

Disposable absorbent articles (such as diapers) include typically an absorbent core structure with superabsorbent polymers, typically hydrogel-forming water-swellable polymers (also referred to as absorbent gelling material, AGM, or super-absorbent polymers, SAP's). This polymer material ensures that in use, large amounts of bodily fluids, e.g. urine, can be absorbed by the article and locked away, thus providing low rewet and good skin dryness.

These water-swellable or superabsorbent polymers need to have adequately high sorption capacity, as well as adequately high gel strength. Sorption capacity needs to be sufficiently high to enable the absorbent polymer to absorb significant amounts of the aqueous body fluids encountered during use of the absorbent article. Together with other properties of the gel, gel strength relates to the tendency of the swollen polymer particles (i.e. gel) to resist deformation under an applied stress in the absorbent article. The gel strength needs to be high enough in the absorbent article so that the particles do not deform too much and thereby fill the capillary void spaces to an unacceptable degree, which would cause so-called gel blocking. This gel-blocking inhibits the rate of fluid uptake and/or the fluid distribution: i.e. once gel-blocking occurs, it can substantially impede the distribution of fluids to relatively dry zones or regions in the absorbent article; then, leakage from the absorbent article can take place well before the superabsorbent polymer particles are fully saturated or before the fluid can diffuse or wick past the "blocking" particles into the rest of the absorbent article. Thus, it is important that the superabsorbent polymers (when incorporated in an absorbent structure or article) maintain a high wet-porosity and have a high resistance against deformation thus yielding high permeability for fluid transport through the swollen gel bed.

Absorbent polymers with relatively high permeability can be made by increasing the level of internal crosslinking or surface crosslinking, which increases the resistance of the swollen gel against deformation by an external pressure (such as the pressure caused by the wearer), but these techniques typically also reduce the absorbent capacity of the gel undesirably.

In addition, there is also a need for superabsorbent polymer particles that have a greater speed of absorption. It has been found that the prior art superabsorbent polymers that may have high gel strength, may often not have a high absorption speed.

In recent years, so-called core-shell superabsorbent polymer particles have been developed that have a superabsorbent polymer core and a shell of elastomeric and/or film-forming polymers, that form an elastomeric shell on the surface of the core, which is elastomeric when dry and when wet, and that reduces deformation of the core-shell particles and that thereby improve the gel strength, whilst having excellent absorbent capacity and speed. For example U.S. Pat. No. 7,049,000 and U.S. Pat. No. 7,270,881 describe such core-shell superabsorbent polymers with an elastic, film-forming thermoplastic polymer shell. However, some of said thermoplastic elastomers may be difficult to process because they may be tacky. Also, some other elastomeric polymers may be hydrophobic.

The inventors have now found alternative coatings for superabsorbent polymer particles, that improve the resistance to deformation (when swollen and under pressure) of said particles when wet, resulting in an improved gel strength, whilst providing excellent absorbent capacity and speed of absorption, and liquid retention under pressure. Said coated superabsorbent particles may furthermore be produced by commercially viable processes.

SUMMARY OF THE INVENTION

The present invention provides a superabsorbent material, comprising first superabsorbent polymers, coated with second clay-crosslinked superabsorbent polymers, said second clay-crosslinked superabsorbent polymers being obtainable by the step of polymerization of a solution or dispersion of polymerizable compounds, in the presence of a dispersion of clay particles, to obtain said second clay-crosslinked superabsorbent polymers, whereby said polymers are crosslinked by said clay particles, and whereby said clay particles having a weight average largest particle dimension of less than 800 nm, between 10 nm and 100 nm, and/or said clay being in the form of individual clay particles, e.g. platelets, as described below.

In one embodiment herein, said coated first superabsorbent polymers are obtainable by the process of:
a) providing said first superabsorbent polymers in solid form;
b) providing a dispersion/solution of said polymerizable compounds and of said clay particles, typically such a homogeneous dispersion as described herein below;
c) applying said dispersion/solution of step c) on said particles of step a), thereby i) polymerizing said compounds, to form polymers, and simultaneously crosslinking said polymers with said clay particles, to form said second clay-crosslinked superabsorbent polymers, and ii) forming a coating of said compounds and said clay, and/or second clay-crosslinked polymers on said particles of a); and
d) drying the resulting coated material of step d), to obtain said coated first superabsorbent polymers;
e) optionally, post-treating of the resulting first coated superabsorbent polymers of step d).

The invention also relates to said process above.

"Dispersion/solution" means herein that each compound or ingredient is either dissolved or dispersed in a liquid. It should be understood that said polymerizable compounds and said clay are typically present in, or combined into, one liquid prior to said coating step, whereby said polymerizable compounds are typically dissolved (hence a solution of said polymerizable compounds), whilst said clay particles are dispersed (hence a dispersion). This is herein referred to as a "solution/dispersion".

Said clay dispersion is typically homogeneous, and/or typically with little or no aggregation of said clay particles. Typically that the clay is at least partially exfoliated or substantially completely, or completely, exfoliated in said dispersion, as described further below.

Said coated first superabsorbent material is typically in solid form, and typically in particulate form, in the form of particles, having a core of said first superabsorbent polymers, coated with said second clay-crosslinked superabsorbent polymers.

Said polymerizable compounds have, in one embodiment herein, a charged group and/or precursor thereof, and said resulting second polymers have a charged group and/or precursor thereof.

Said second clay-crosslinked superabsorbent polymers provide a stretchable coating that can stretch when the first superabsorbent polymer particle swells, providing resistance to deformation under pressure of said swollen superabsorbent particles. Furthermore, the coating made of said second clay-crosslinked superabsorbent polymers provides additional absorbency. Furthermore, the hydrophilic nature of said clay present in said second clay-crosslinked superabsorbent polymers, and/or the hydrophilic nature of said second clay-crosslinked superabsorbent polymers, in particular when having charged (e.g. anions groups) renders the coating therewith hydrophilic, which improves the absorbency/absorbency speed of said superabsorbent material and its capability to de-water adjacent layers of the absorbent article via capillary pressure.

Said first superabsorbent polymers and/or second clay-crosslinked superabsorbent polymers are (e.g. anionic) polyelectrolyte polymers which comprise typically "free" ions, for example sodium ions. The polymers may be polyacrylates.

Some polymers cross-linked by nano-sized clay particles are know in the art to form elastic or stretchable hydrogels. For example, water-containing hydrogel shaped or molded articles, comprising certain specific isopropyl polyamides cross-linked by certain clay particles are described in *Macromolecules* 2002, 35, 10162-10171 (Kazutoshi Haraguchi et all); these elastic, shaped hydrogels are intended for medical purposes where they can be used in applications where they can de-water quickly, and thus shrink, upon demand, e.g. driven by temperature changes. WO09/041870 and WO2009/041903 describe the need to make clay-linked polyacrylates, which provide a better absorbency, but that acrylates cannot be used to form polymers that are linked by nano-size clay particles successfully, because the clay aggregates (agglomerates) in the presence of acrylate and acrylic acid. They teach thereto fibers, foams and gels (that may be made in particles) of clay-linked hydrogels, made by mixing nano-size clay particles and acrylic esters in a liquid, to form polyacrylic esters that are clay-linked, and then shaping this into for example foams or fibers or gel blocks. This can then be hydrolyzed to obtain such shapes of clay-linked polyacrylates.

However, the hydrolyses of complete foams, fibers or gels, or even batches of finished particles of polyacrylic esters is a very slow and energy-demanding process, because the penetration of the hydrolysis solution is driven by diffusion only which is a generally slow process, in particular if larger shapes such as foams or gels need to be hydrolyzed (internally). Furthermore, hydrolysis of ground particles would cause the particles to form a gel blocks (the particles would stick together due to the hydrolysis solvent liquid), which would then need to be dried and ground, sieved etc. to obtain particles. Thus, the proposed clay-crosslinked polyester gel blocks and foams, or even fibers or particles, and the hydrolysis thereof are not suitable for commercial scale production of clay-linked polyacrylates (particles).

The present invention does not suffer from these drawbacks, because the second clay-crosslinked superabsorbent polymers, which are polymers cross-linked by nano-sized clay particles, are only present as a thin coating on the surface of other (first) superabsorbent material (that is not clay-crosslinked and that is typically not a neutral polymer, like a polyester, that need to be hydrolyzed in order to obtain a charged polymer) and because they are not intended to provide the absorbent capacity of the superabsorbent material (which is primarily provided by said first superabsorbent polymer particles). Hence, only a very thin coating needs to be briefly subjected to hydrolysis. Furthermore, no complete hydrolysis of the coating, or even no hydrolysis at all, is needed to obtain suitable superabsorbent material. Furthermore, the coating will even provide the required elastic properties, hydrophilic properties when partially hydrolyzed, or even when not hydrolyzed at all.

Said coating of said second clay-crosslinked superabsorbent polymers on said first superabsorbent polymers in solid form has an average caliper of from 2 microns to 20 microns, or to 10 microns. The coating is homogeneous, including having a homogeneous composition and a homogeneous/uniform caliper, as described below.

Said superabsorbent material and/or said coated superabsorbent polymer particles are for example in the form of particles having a weight average particle size of from 200 to 800 microns.

DETAILED DESCRIPTION

"Superabsorbent material" and "superabsorbent polymers" or "superabsorbent polymer particles" as used herein, refers to a material, or to polymers or particles that absorbs and retains at least 10 grams of saline (0.9% saline solution in de-mineralized water), per gram of superabsorbent material, or polymers or particles, as measurable by the CRC method set out herein. Obviously, it will absorb other aqueous liquids as well, such as urine, blood.

The superabsorbent material, and the superabsorbent polymers and superabsorbent polymer particles herein are water-swellable e.g. such that they swell in a 0.9% saline solution in demineralised water, by absorbing the said saline water; they may thereby form a gel. Obviously, the superabsorbent material/polymers herein swell in other liquids, like urine and blood as well.

The superabsorbent material herein comprises said coated superabsorbent polymers, which are in solid form, typically in particulate form—herein referred to as "particles", but it may also contain other materials (including superabsorbent polymer particles that are not coated with the second clay-crosslinked superabsorbent polymers herein). However, the coated superabsorbent polymers (particles) herein are present at a level of at least 20% by weight (of the superabsorbent material), more from 50% to 100% by weight or even from 80% to 100% by weight, and most between 90% and 100% by weight of said superabsorbent material.

The coating of said second clay-crosslinked superabsorbent polymers (e.g. particles) is applied such that the resulting coating or coating layer is thin; for example, the coating (layer) has an average calliper (thickness) between 1 micron ($\mu$m) and 100 microns, from 1 micron to 50 microns, more from 1 micron to 20 microns or even from 2 to 20 microns or even from 2 to 10 microns.

The coating (layer) is uniform in calliper and/or shape. The average calliper is such that the ratio of the smallest to largest caliper is from 1:1 to 1:5, from 1:1 to 1:3, or even 1:1 to 1:2, or even 1:1 to 1:1.5.

The weight average coating caliper may for example be of from 1 or 2 to 20 µm, 1 or 2 to 10 µm.

Said coating may be present at a weight level of for example from 0.05% to 30% by weight of the coated particles, more from 0.5% to 20% or to 10% or to 15%.

The superabsorbent material is typically in solid form, and typically in the form of a gel, film, or foam, or in particulate form, which include for the purpose of the invention flakes, fibers, agglomerates, blocks, granules, particles, spheres. The superabsorbent material and/or the coated superabsorbent polymer particles herein, is in the form of particles having a mass median particle size up to 2 mm, or even between 50 microns and 1 mm, or between 100 µm and 800 µm, as can for example be measured by the method set out in for example EP-A-0691133.

In one embodiment of the invention the superabsorbent material and/or the superabsorbent coated polymer particles of the invention are in the form of ("free" flowing) particles with particle sizes between 10 µm and 1200 µm or even between 50 µm and 800 µm and a mass median particle size between 100 or 200 and 800 µm or 600 µm.

In addition, or in another embodiment of the invention, said particles are essentially spherical.

In yet another or additional embodiment of the invention the superabsorbent material and/or coated superabsorbent polymer particles of the invention have a relatively narrow range of particle sizes, e.g. with the majority (e.g. at least 80% or at least 90% or even at least 95%) of particles having a particle size between 50 µm and 800 µm, between 100 µm and 600 µm, and more between 200 µm and 600 µm.

The superabsorbent material and/or coated superabsorbent polymer particles of the invention comprise less than 15% by weight of water, or less than 10%, or less than 8% or less than 5%, or no water. The water-content can be determined by the Edana test, number ERT 430.1-99 (February 1999) which involves drying the superabsorbent material at 105° Celsius for 3 hours and determining the moisture content by the weight loss of the superabsorbent materials after drying.

Superabsorbent materials the invention have a high sorption capacity measured by the commonly used Centrifugation Retention Capacity test, CRC, (as described below); said CRC being at least 10 g/g, but at least 20 g/g, or at 30 g/g. Upper limits may for example be up to 150 g/g, or up to 100 g/g/or up to 80 g/g.

Superabsorbent materials of the invention have a good permeability for liquid, for example, having a SFC value of at least $10 \times 10^{-7}$ cm$^3$ s/g; or at least $30 \times 10^{-7}$ cm$^3 \cdot$s/g, or at least $50 \times 10^{-7}$ cm$^3$ s/g $10 \times 10^{-7}$ cm$^3$ s/g, or possibly permeability SFC value of at least $100 \times 10^{-7}$ cm$^3$ s/g, or at least a SFC of $120 \times 10^{-7}$ cm$^3$ sec/g. This SFC is a measure of permeability and an indication of porosity is provided by the saline flow conductivity of the gel bed as described in U.S. Pat. No. 5,562,646, (Goldman et al.) issued Oct. 8, 1996 (whereby however a 0.9% NaCl solution is used instead of Jayco solution). Upper limits may for example be up to 350 or $250 \times 10^{-7}$ cm$^3 \cdot$s/g.

The superabsorbent material of the invention may be used in an absorbent structure, together with (mixed with) other materials, such as fibers, (fibrous) glues, organic or inorganic filler materials or flowing aids, process aids, anti-caking agents, odor control agents, colouring agents, coatings to impart wet stickiness, hydrophilic surface coatings, other superabsorbent polymer particles, not comprising a coating of said second clay-crosslinked superabsorbent polymers herein, etc. This is described in more detail below.

First Superabsorbent Polymers and Cores and Particles Thereof

The first super absorbent polymers herein are coated with a coating of second clay-crosslinked superabsorbent polymers, described below; the first superabsorbent polymers are thereto typically in solid, e.g., in the form of particles (which includes flakes, fibers, agglomerates, blocks, granules, particles, spheres).

The superabsorbent polymers typically form the core of the solid, e.g. particulate coated superabsorbent polymers herein, said core then being coated with said second superabsorbent polymers described herein below. In one embodiment, the first superabsorbent polymers are in the form particles having a mass median particle size as specified above for the superabsorbent material. The first superabsorbent polymer particles (e.g. cores) may have the mass median particle sizes and distributions as cited above for the coated particles and superabsorbent materials, plus the thickness (calliper) of the coating; however, when for the purpose of the invention, the coating thickness is neglectable (for example being 2 to 20 microns), the first superabsorbent polymer particles typically have a mass median particle size/distribution which is the same as those cited above for the coated material.

The first superabsorbent polymers are typically (lightly) crosslinked polymers.

The first superabsorbent polymers may in general be non-ionic, cationic, zwitterionic, or anionic, the polymers are polyelectrolytes, anionic polyelectrolyte polymers. Especially suitable are (salts of) acid polymers, which contain a multiplicity of acid functional groups such as a carboxylic acid groups. Examples of (salts of) acid polymers suitable for use herein include those which are prepared from polymerizable, acid-containing monomers, or salts thereof. The superabsorbent polymers can also comprise polymers that are not prepared from olefinically unsaturated monomers. Examples of such polymers also include polysaccharide-based polymers such as carboxymethyl starch and carboxymethyl cellulose, and poly(amino acid) based polymers such as poly(aspartic acid). For a description of poly(amino acid) absorbent polymers, see, for example, U.S. Pat. No. 5,247,068, issued Sep. 21, 1993 to Donachy et al. Some non-acid monomers can also be included, usually in minor amounts, in preparing the first superabsorbent polymers herein. Such non-acid monomers can include, for example, monomers containing the following types of functional groups: carboxylate esters, sulfonate esters, hydroxyl groups, amide-groups, amino groups, nitrile groups, quaternary ammonium salt groups, and aryl groups (e.g., phenyl groups, such as those derived from styrene monomer). Other optional non-acid monomers include unsaturated hydrocarbons such as ethylene, propylene, 1-butene, butadiene, and isoprene. These non-acid monomers are well-known materials and are described in greater detail, for example, in U.S. Pat. No. 4,076,663 (Masuda et al.), issued Feb. 28, 1978, and in U.S. Pat. No. 4,062,817 (Westerman), issued Dec. 13, 1977.

Olefinically unsaturated carboxylic acid useful herein include the acrylic acids typified by acrylic acid itself, methacrylic acid, α-chloroacrylic acid, α-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citroconic acid, mesaconic acid, glutaconic acid, aconitic acid, maleic acid, fumaric acid, tricarboxyethylene, and maleic anhydride.

Particularly suitable first superabsorbent polymers are polyacrylates/acrylic acids and derivatives thereof, (slightly) network crosslinked, partially neutralized polyacrylic acids, and/or optionally, starch derivatives thereof.

Polymers herein may contain carboxyl groups, such as the above-described carboxylic acid/carboxylate containing groups. These polymers include hydrolyzed starch-acrylonitrile graft copolymers, partially neutralized hydrolyzed starch-acrylonitrile graft copolymers, starch-acrylic acid graft copolymers, partially neutralized starch-acrylic acid graft copolymers, hydrolyzed vinyl acetate-acrylic ester copolymers, hydrolyzed acrylonitrile or acrylamide copolymers, slightly network crosslinked polymers of any of the aforementioned copolymers, polyacrylic acid, and slightly network crosslinked polymers of polyacrylic acid. These polymers can be used either solely or in the form of a mixture of two or more different polymers. Examples of these polymer materials are disclosed in U.S. Pat. No. 3,661,875, U.S. Pat. No. 4,076,663, U.S. Pat. No. 4,093,776, U.S. Pat. No. 4,666,983, and U.S. Pat. No. 4,734,478.

The first superabsorbent polymers are partially neutralized polymeric acrylic acid, partially in the form of sodium salt thereof.

It should be understood that the first superabsorbent polymers are free of said nano-sized clay particles, as described below for said second clay-crosslinked superabsorbent polymers. Thus, said first superabsorbent polymer and said second clay-crosslinked superabsorbent polymers are different to one another, said difference being at least the absence or presence, respectively, of said clay particles, (that in the latter case crosslink said second superabsorbent polymers).

As mentioned above, he first superabsorbent polymers are organically crosslinked, as known in the art. (whilst, in one embodiment, the second clay-crosslinked superabsorbent polymers are not crosslinked by any compound other than said clay particles.) The first superabsorbent polymers useful in the present invention can be formed by any polymerization and/or crosslinking techniques. Typical processes for producing these polymers are described in U.S. Reissue Pat. No. 32,649 (Brandt et al.), issued Apr. 19, 1988, U.S. Pat. No. 4,666,983 (Tsubakimoto et al.), issued May 19, 1987, and U.S. Pat. No. 4,625,001 (Tsubakimoto et al.), issued Nov. 25, 1986; U.S. Pat. No. 5,140,076 (Harada); U.S. Pat. No. 6,376,618 B1, U.S. Pat. No. 6,391,451 and U.S. Pat. No. 6,239,230 (Mitchell); U.S. Pat. No. 6,150,469 (Harada). Crosslinking can be affected during polymerization by incorporation of suitable crosslinking monomers. Alternatively, the polymers can be organically crosslinked after polymerization by reaction with a suitable reactive crosslinking agent. Crosslinking renders the polymer substantially water-insoluble and, in part, determines the absorptive capacity and extractable polymer content characteristics of the absorbent polymers. Processes for crosslinking these polymers and typical bulk crosslinking agents are described in greater detail in U.S. Pat. No. 4,076,663.

The organic crosslinkers as useful herein are compounds having at least two free-radically polymerizable groups which can be free-radically interpolymerized into the polymer network. Useful crosslinkers b) are for example ethylene glycol dimethacrylate, diethylene glycol diacrylate, allyl methacrylate, trimethylolpropane triacrylate, triallylamine, tetraallyloxyethane, as described in EP-A-0 530 438, di- and triacrylates as described in EP-A-0 547 847, EP-A-0 559 476, EP-A-0 632 068, WO-A-93/21237, WO-A-03/104299, WO-A-03/104300, WO-A-03/104301 and DE-A-103 31 450, mixed acrylates which, as well as acrylate groups, comprise further ethylenically unsaturated groups, as described in DE-A-103 314 56 and prior German application 10355401.7, or crosslinker mixtures as described for example in DE-A-1 95 43 368, DE-A-1 96 46 484, WO-A-90/15830 and WO-A-02/32962.

Useful crosslinkers include in particular N,N'-methylenebisacrylamide and N,N'-methylenebismethacrylamide, esters of unsaturated mono- or polycarboxylic acids of polyols, such as diacrylate or triacrylate, for example butanediol diacrylate, butanediol dimethacrylate, ethylene glycol diacrylate, ethylene glycol dimethacrylate and also trimethylolpropane triacrylate and allyl compounds, such as allyl (meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP-A-0 343 427. Useful crosslinkers b) further include pentaerythritol diallyl ether, pentaerythritol triallyl ether, pentaerythritol tetraallyl ether, polyethylene glycol diallyl ether, ethylene glycol diallyl ether, glycerol diallyl ether, glycerol triallyl ether, polyallyl ethers based on sorbitol, and also ethoxylated variants thereof. The process of the present invention may utilize di(meth)acrylates of polyethylene glycols, the polyethylene glycol used having a molecular weight between 300 and 1000.

Advantageous crosslinkers b) include di- and triacrylates of 3- to 15-tuply ethoxylated glycerol, of 3- to 15-tuply ethoxylated trimethylolpropane, of 3- to 15-tuply ethoxylated trimethylolethane, especially di- and triacrylates of 2- to 6-tuply ethoxylated glycerol or of 2- to 6-tuply ethoxylated trimethylolpropane, of 3-tuply propoxylated glycerol, of 3-tuply propoxylated trimethylolpropane, and also of 3-tuply mixed ethoxylated or propoxylated glycerol, of 3-tuply mixed ethoxylated or propoxylated trimethylolpropane, of 15-tuply ethoxylated glycerol, of 15-tuply ethoxylated trimethylolpropane, of 40-tuply ethoxylated glycerol, of 40-tuply ethoxylated trimethylolethane and also of 40-tuply ethoxylated trimethylolpropane. Suitable crosslinkers b) may be diacrylated, dimethacrylated, triacrylated or trimethacrylated multiply ethoxylated and/or propoxylated glycerols; in particular di- and/or triacrylates of 3- to 10-tuply ethoxylated glycerol or di- or triacrylates of 1- to 5-tuply ethoxylated and/or propoxylated glycerol or triacrylates of 3- to 5-tuply ethoxylated and/or propoxylated glycerol.

In one embodiment, the organic crosslinking agent is a hydrophilic organic crosslinking agent may also be used in herein. Examples include polyhydric alcohols such as ethylene glycol, diethylene glycol, triethylene glycol, tetraethylene glycol, polyethylene glycol, glycerol, polyglycerol, propylene glycol, diethanolamine, triethanolamine, polyoxypropylene, oxyethylene oxypropylene block copolymer, pentaerythritol and sorbitol; polyglycidyl compounds such as ethylene glycol diglycidyl ether, polyethylene glycol diglycidyl ether, glycerol polyglycidyl ether, diglycerol polyglycidyl ether, polyglycerol polyglycidyl ether, sorbitol polyglycidyl ether, pentaerythritol polyglycidyl ether, propylene glycol diglycidyl ether and polypropylene glycol diglycidyl ether; polyvalent aziridines such as 2,2-bishydroxymethyl butanol-tris[3-(1-aziridinyl)-propionate], 1,6-hexamethylenediethyleneurea and diphenylmethane-bis-4, 4'-N,N'-diethyleneurea; haloepoxy compounds such as epichlorohydrin and alpha-methylchlorohydrin; polyvalent aldehydes such as glutaraldehyde and glyoxal; polyamines such as ethylenediamine, diethylenetriamine, triethylenetetramine, tetraethylenepentamine, pentaethylenehexamine and polyethyleneimine; polyisocyanates such as 2,4-toluylene diisocyanate and hexamethylene diisocyanate; polyvalent metal salts such as aluminum chloride, magnesium chloride, calcium chloride, aluminum sulfate, magnesium sulfate and calcium sulfate; and alkyl di(tri)halogenides such as 1,4-dibromobutane, 1,6-dibromohexane and 1,3,5-trichloropentane.

Suitable amounts of crosslinking agent useful herein are generally between 0.005 to 5% by weight based on the first superabsorbent polymers.

The first superabsorbent polymers may also be surface-crosslinked, prior to, simultaneously with or after the coating step herein. However, in one embodiment herein, said surface cross-linking is not needed and not present, in view of said coating of said second clay-crosslinked superabsorbent polymers.

The first superabsorbent polymers comprise 50% to 95% (mol percentage), about 75 mol %, neutralized (slightly) crosslinked polyacrylic acid, having sodium counter ions (e.g. poly (sodium acrylate/acrylic acid)).

The first superabsorbent polymers have a low amount of extractables, less than 15% (by weight of the polymers), less than 10% and less than 5% of extractables, or even less than 3% (values of 1 hour test). The extractables and levels/determination thereof can be measured by the test referred to below.

While the superabsorbent polymer is of one type (i.e., homogeneous), mixtures of superabsorbent polymers can also be used in the present invention. For example, mixtures of starch-acrylic acid graft copolymers and slightly network crosslinked polymers of polyacrylic acid can be used in the present invention. Mixtures of (coated) polymers with different physical properties, and optionally also different chemical properties, could also be used, e.g. different mean particle size, absorbent capacity CRC, SFC value.

Second Clay-Crosslinked Superabsorbent Polymer, Polymerizable Compounds and Polymerization Thereof The second clay-crosslinked superabsorbent polymers herein are formed by polymerizing polymerizable compounds (e.g. monomers) in the presence of clay particles, specified below, so that said clay particles crosslink said polymers. The resulting second clay-crosslinked polymers are herein referred to as second clay-crosslinked superabsorbent polymers. It is thus essential that said clay particles are present during the polymerisation of said polymerizable compounds (efficient and/or endurable cross-linking cannot be achieved by admixing the clay particles into a dispersion of the final polymers, after polymerization).

The polymerizable compounds may comprise repeating units of monomer groups, for example the polymerizable unit may be a di-mer. However, in one embodiment herein, the polymerizable compounds are monomers.

Said polymerization is typically done in a carrier liquid and/or on the surface of the solid first superabsorbent polymers, in which the polymerizable compounds are dispersed or typically dissolved and said clay particles are typically dispersed. Any of such combination of said compounds and clay particles in a carrier liquid is herein referred to as "dispersion and/or solution".

Without wishing to be bound by theory, it is believed that such superabsorbent material, whereby said polymers are linked via said nano-sized clay particles, have a narrower distribution of the polymer chain segments between two cross-linking points (e.g. two clay particles). It is thus believed that said polymer chain segments are of similar chain length and that they are hence able to (substantially) all move and expand to a similar extend when the coated superabsorbent polymer particles swell due to fluid-absorption. It is believed that mechanistically, the polymers connected to the same clay particle sustain a force (stretching or pressure) cooperatively and hence avoid or reduce stress localization and chain tearing under deformation; this then can increase the elongation to break compared to traditional crosslinked polymer networks, whereby the crosslinking is achieved by organic crosslinking groups. This is believed to ensure that the coating can stretch and expand upon swelling, without significant tearing, and can prevent or reduce deformation and hence reduce gel blocking. Furthermore, it is believed that such coatings of such second clay-crosslinked superabsorbent polymers provide a high absorption speed, due to the hydrophilic nature of the clay particles, and typically of the polymers used, in particular when partially or completely hydrolyzed, as described below.

Furthermore, due to the superabsorbent properties of the coating material, the fluids to be absorbed (e.g. bodily fluids) are readily absorbed by the coating and then by the first superabsorbent polymers (e.g. in the core).

It should be noted that, unlike the elastomeric film-forming polymers of U.S. Pat. No. 7,049,000 and U.S. Pat. No. 7,270,881, referred to in the "background" section, the polymers of the second clay-crosslinked superabsorbent polymers (after hydrolysis, if applicable) are (typically) not elastomeric in dry state, and/or said polymers have in dry state a Tg of at least 40° C., or at least 60° C., or at least 80° C., or at least 100° C. (as measurable by the method set out in the references above). Thus, in wet state, the coating herein may be stretchable, but in one embodiment, the polymers of said coating are not elastomeric and/or have the higher Tg's cited above.

The polymerizable compounds, e.g. monomers, are thus chosen such that the resulting polymers, after hydrolysis if applicable, are not elastomeric in dry state and/or have a Tg, as described above.

In general, it is believed that polyelectrolyte polymers provide the required osmotic pressure that drives the required absorption and retention of fluids like urine. Thus, in order to further increase the capacity of the coated superabsorbent polymers and superabsorbent material herein, the second clay-crosslinked superabsorbent polymers are polyelectrolytes, and even more anionic polymers.

Thus, in one embodiment herein, said second clay-crosslinked superabsorbent polymers herein are for example made by polymerizing polymerizible compounds, e.g. monomers, which have a charged group, or precursor group thereof, an anionic group or a precursor thereof, or a mixture of compounds (monomers) with a cationic group or precursor thereof, and compounds (monomers) with an anionic group or precursor thereof. (Such groups are pending from the polymer backbone.)

It should be understood that for the purpose of the invention that a group that has an acid and base form, such as a carboxylic acid group, is herein considered a charged group, since it would in the dispersion/solution used herein be at least partially in its charged form, e.g. carboxylate form.

In one embodiment the polymerizable compounds have cationic group- and/or anionic group-precursor groups, said precursor groups being neutral. Said anionic or cationic group precursor group should be readily made into anionic or cationic groups during or typically after the polymerization reaction, by for example hydrolysis. If the polymerizable compounds comprise an anionic precursor group, the polymerization reaction herein comprises the step of forming said precursor group into an anionic group, for example by hydrolysis.

In one embodiment herein, the anionic group herein is a carboxylate group or carboxylic acid group, as defined herein. In such an embodiment, a suitable anionic precursor group for the polymerizable compound would be for example an amide or an ester group; it may be for example an ester group, such as a methyl or ethyl ester, because such ester groups are easier to hydrolyse than amide groups. Exemplary second clay-crosslinked polyamide polymers are for example described in EP1160286. Exemplary second clay-crosslinked polyester polymers are for example described in EP1589038.

However, in one embodiment herein, hydrolysis is avoided, and the polymerizable compounds include or consist of compounds that have a charged group, an anionic charged group, which includes, as set out herein, acids forms of such anionic groups, and/or base forms of such cationic groups.

In one embodiment herein, said second clay-crosslinked superabsorbent polymers are typically made in a manner whereby said partly or substantially completely exfoliated clay dispersion and said dispersion/solution of said polymerizable compound are only combined at the coating, e.g. spraying step, or just before said coating step, (spraying step), such as within 30 seconds, or within 20 second or within 10 seconds of said spraying step, and said polymerization is only started at the coating/spraying step or just before the coating/spraying step, and said the polymerization commences immediately upon initiation coating. Because of this, polymerization is fast and can take place before significant aggregation of the clay particles can take place. Hence, charged polymerizable compounds may be employed without the risk of significant aggregation.

The second clay-crosslinked superabsorbent polymers herein may comprise "free" ions, or "free" cations, such as sodium ions.

In one embodiment herein, said second clay-crosslinked superabsorbent polymers herein are for example made by polymerizing polymerizible compounds, e.g. monomers, whereof at least 80% or at least 90% or even 100% by weight are polymerizable compounds, e.g. monomers, which have an anionic group (or before hydrolysis: a precursor thereof). Thus, in such an embodiment, the final polymer may comprise monomer units that do not have an anionic group, but only to a minor extend, e.g. less than about 20%, or less than 10% by weight.

For example, at least 80%, or at least 90% or even 100% of the polymerizable compounds, e.g. monomers, are compounds with a cationic and/or anionic group.

In one embodiment, at least 80%, or at least 90% or even 100% of the polymerizable compounds, e.g. monomers, have no substituent groups other than said charged group or charged-group-precursor thereof. S charged group is an anionic group having at the most two carbon atoms, or being a carboxylate group. This will provide polymers that have no hindering substituent groups and therefore a greater chain movement flexibility; this is believed to improve the greater absorption (diffusion speed) and absorption capacity.

The polymerizable compounds may be polymerizable by any type of polymerization reaction, by use of a polymerization initiator that is activated, to initiate the polymerization. In one embodiment herein, the polymerization reaction is a free radical reaction, and said polymerizable compounds, e.g. monomers, comprise therefore groups that can form chemical bonds with one another in a radical reaction.

Such a free radical polymerization reaction typically takes place in the presence of a radical initiator, as described below. The monomers may comprise an unsaturated group, e.g. a C=C group.

Monomers herein may include ethylene oxide; propylene oxide; ethylenimine; but typically olefinically unsaturated carboxylates and/or carboxylic acids, and/or amides or esters thereof, although said amides and esters may not be preferred in one embodiment herein, as described herein; for example selected acrylic acids typified by acrylic acid itself, methacrylic acid, α-chloroacrylic acid, α-cyanoacrylic acid, β-methylacrylic acid (crotonic acid), α-phenylacrylic acid, β-acryloxypropionic acid, sorbic acid, α-chlorosorbic acid, angelic acid, cinnamic acid, p-chlorocinnamic acid, β-stearylacrylic acid, itaconic acid, citroconic acid, mesaconic acid, glutaconic acid, aconitic acid, maleic acid, fumaric acid, tricarboxyethylene, and maleic anhydride; and/or any of the carboxylates of these polymerizable compounds, e.g. carboxylate salts.

It may particularly desirable for the polymerizable compounds to include or consist of acrylic acids and/or acrylate salts (and/or precursors thereof, such as typically acrylic esters); or in one embodiment herein, acrylic ester polymerizable compounds; anionic group precursors may include methoxyethyl esters (e.g. acrylic ester), ethoxyethyl esters (e.g. acrylic ester), methyl esters (e.g. acrylic ester), and ethyl esters (e.g. acrylic ester).

It should be understood that polymerizable compounds that do not have an anionic group or precursor thereto, may be used herein. Such compounds can include, for example, monomers containing the following types of functional groups: hydroxyl groups, amino groups, and aryl groups (e.g., phenyl groups, such as those derived from styrene monomer). Other optional polymerizable monomers that may be used in addition include unsaturated hydrocarbons such as ethylene, propylene, 1-butene, butadiene, and isoprene. These non-acid monomers are well-known materials and are described in greater detail, for example, in U.S. Pat. No. 4,076,663 (Masuda et al.), issued Feb. 28, 1978, and in U.S. Pat. No. 4,062,817 (Westerman), issued Dec. 13, 1977.

A polymerization initiator and/or catalyst may be used; they can be appropriately selected from conventional (radical) polymerization initiators and catalysts. Materials which display good water dispersibility/solubility may be particularly suitable.

In one embodiment herein, at least a polymerization initiator is used to initiate the polymerization. This may include a so-called initiator system, comprising more than one compound to initiate the polymerization.

The initiator may need to be activated in order to initiate polymerization, or no activation may be needed. In one embodiment, the initiator is activated during the spraying step, or upon entry into the vessel, by known activation methods, including heat or radiation.

They can be appropriately selected from conventional (radical) polymerization initiators and catalysts. The polymerization reaction is a radical polymerization reaction and a radical polymerization initiator is present, selected from peroxides, hydroperoxides, hydrogen peroxide, persulfates, azo compounds and redox initiators. Useful organic peroxides are for example acetylacetone peroxide, methyl ethyl ketone peroxide, tert-butyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butyl permaleate, tert-butyl perbenzoate, di(2-ethylhexyl) peroxydicarbonate, dicyclohexyl peroxydicarbonate, di(4-tert-butylcyclohexyl) peroxydicarbonate, dimyristyl peroxydicarbonate, diacetyl peroxydicarbonate, allyl peresters, cumyl peroxyneodecanoate, tert-butyl per-3,5,5-tri-methylhexanoate, acetylcyclohexylsulfonyl peroxide, dilauryl peroxide, dibenzoyl peroxide and tert-amyl perneodecanoate. Suitable azo compounds include 2,2'-azobisisobutyronitrile, 2,2'-azobis(2,4-dimethylvaleronitrile) and 2,2'-azobis(4-methoxy-2,4-dimethyl-valeronitrile), especially water-soluble azo initiators, examples being 2,2'-azobis-{2-[1-(2-hydroxyethyl)-2-imidazolin-2-yl]propane}dihydrochloride, 2,2'-azobis-(2-amidinopropane) dihydrochloride, 2,2'-azobis[2-(2-imidazolin-2-yl)propane]dihydrochloride and 2,2'-azobis[2-(5-methyl-2-imidazolin-2-yl)propane]dihydrochloride. 2,2'-azobis[2-(2-imidazolin-2-yl)propane]dihydrochloride and 2,2'-azobis[2-(5-methyl-2-imidazolin-2-yl)propane]dihydrochloride may be particularly suitable for use herein.

Persulfates such as sodium peroxodisulfate, potassium peroxodisulfate and ammonium peroxodisulfate; hydroperoxides such as t-butyl hydroperoxide and cumene hydroperoxide; and azo compounds such as 2,2'-azobis-2-amidinopropane hydrochloride, e.g. such as VA-044, V-50 and V-501 (all manufactured by Wako Pure Chemical Industries Ltd.), and mixtures of $Fe^{2+}$; and hydrogen peroxide, or hydrogen peroxide and ascorbic acid. The latter may be suitable initiator system for use herein.

The polymerization initiator may be used per se, and then it may for example be added to the carrier liquid with polymerizable compounds (monomers) and/or to the clay particle dispersion; or it may be used as a dispersion or solution. It may be added just prior to the coating/spraying step or during the coating/spraying step. It may be added in the form of a dispersion/solution in a carrier liquid, which is the same as the carrier liquid of the polymerizable compounds and/or of the clay particles.

In one embodiment, a mixture of two or more polymerization initiators is used, for example one of the class of azo-compounds and one of the class of peroxo or peroxide compounds, as described above. This is believed to ensure fast polymerization.

In order to increase the polymerization speed, the polymerization initiator may for example be introduced onto the polymerization reaction liquid at a level of for example at least 0.1% by weight of the polymerizable compounds, or for example at least 0.3% or at least 0.5% or at least 0.7%, up to typically 10% or 5% or 3% by weight.

The polymerization rate can be controlled through the identity and amount of the initiator system used. As for example described in US2008/242817, the use of azo compound initiator or redox initiators is advantageous for directing the rate of polymerization.

For some initiators, no activation is needed; other initiators may require activation, as known in the art. The initiator may be activated by any method known in the art, including heat or radiation. Thereto, the dispersions/solutions of the monomer compound and/or clay are cooled (e.g. to a temperature of less than polymerization temperature, e.g. less than 20° C., or less than 10° C.) or and/or shielded from radiation prior to introduction of the initiator, and optionally at the moment of addition of the initiator, and that said combination of initiator and dispersion/solution is exposed to the activation source, e.g. heat, radiation, only at the desired moment, for example upon introduction onto the spraying step/spraying tool or upon introduction into the vessel.

A polymerization catalyst may also be present, such as for example TMEDA, N,N,N',N' tetramethylethylenediamine.

The polymerization reaction takes place in the presence of said clay particles.

Said clay particles form bridging point between said polymers, thereby cross-linking said polymers. Typically, substantially all said polymers are bonded to at least one nano-size clay particle during said polymerization reaction, typically more than one; this may be characterized by determination of the extractable levels of said second clay-crosslinked superabsorbent polymers, by the method described below. The extractable level of the second clay-crosslinked superabsorbent polymers is less than 15% (by weight of said polymers), less than 10% and less than 5% or less than 3% of extractables.

Said clay particles in the second-clay-crosslinked superabsorbent polymer (as coating, but also prior to the polymerization reaction herein, in the dispersion) may have a weight average largest particle dimension of less than 800 nm, less than 500, less than 300 nm, for example up to 200 nm, or up to 100 nm, or up to 70 nm or up to 60 nm or up to 40 nm; and for example a said weight average largest particle size dimension being at least 1 nm, or at least 10, or at least 20 nm. For example individual, exfoliated laponite may be used, having a weight average largest particle dimension of 30 nm. This can be determined by TEM, as described below.

Additionally or alternatively said clay in said second clay-crosslinked superabsorbent polymer coating are substantially all individual clay particles/platelets, and/or said clay in the dispersion is exfoliated clay of individual clay particles/platelets, as can be determined as described below.

The degree of exfoliation of the dispersion, and the related degree of aggregation (or even: absence thereof), can be determined by Cryo-TEM, as described in "Aqueous Dispersions of Silane-Functionalized Laponite Clay Platelets. A first step towards the Elaboration of Water-based Polymer/Clay Nanocomposites" Herrera et al, *Langmuir* 2004, 20, 1564-157.

The dispersion herein, prior to polymerization, has an exfoliation degree of at least 60%, or at least 80% or at least 90% or at least 95% or about 100%, as measurable by XRD.

The absence of aggregation in the dispersion can alternatively be determined via the percentage of individual clay particles/platelets in the final second clay-crosslinked polymers herein, e.g. by use of XRD, or by TEM, as described in "Polyampholytes superabsorbent nanocomposites with excellent gel strength", Kun Xu et al, ScienceDirect, Comparative Science & technology, 67 (2007), 3480-3486 (available via www.science direct.com or www.elsevier.com.)

This is done via removal of a microslice of said second clay-crosslinked superabsorbent polymers coating (via a ultramicrotome) and submitting this to XRD, or TEM.

In one embodiment herein the clay in the second clay-crosslinked superabsorbent polymer is in the form of individual clay particles/platelets, as measurable by TEM, as above. In one embodiment, at least 60%, at least 80% or at least 90% or even 100% of the clay are present as individual clay particles/platelets (in said second clay-crosslinked polymer).

It should be understood that for the purpose of the invention, the particle sizes/level of individual clay particles/platelets are applicable to at least part of the second clay-crosslinked superabsorbent polymer in the coating, but typically to the majority thereof, or to all of the coating. Thus the measurements above are thus done on several, at least 3, representative samples of the clay-linked superabsorbent polymer of the coating, to obtain an average over said samples, which is herein referred to as the average of said polymers as a whole.

In one embodiment, the second clay-crosslinked polymers are homogeneously crosslinked polymers.

Thus, the clays herein may be partially exfoliated in said dispersion; but, in embodiments herein the dispersion is a substantially completely (e.g. >90% by weight) or even completely exfoliated clay dispersion, e.g. at least 90% of the clay (or at least 95% or 100%) the clay being in the form of sheet-like platelets in said dispersion, —herein referred to also as "exfoliated clay dispersion".

The clay particles may be in the form of platelets, e.g. exfoliated or individual clay particles in the form of platelets, having a largest dimension and a smallest dimension, with for example a largest dimension to smallest dimension ratio of at least 2:1, or at least 10:1 or at least 25:1, up to for example 100:1.

As mentioned above, the clay particle dispersion suitable herein is typically a homogeneous dispersion of clay particles and/or it is partly or completely exfoliated clay dispersion. Exfoliation of clay is achievable by methods known in the art, e.g. by applying high shear force, either ultrasonically and/or by high shear force mixing, optionally under heating of the liquid, for example to a temperature above 40° C., or above 45° C. or above 50° C., optionally up to 70° C. or up to 60° C. or up to 55° C. For example, a Y-Tron mixer can be used for wetting the clay with the liquid, e.g. aqueous liquid or water, and keep re-circulating the dispersion for 20-30 minutes through the Y-Tron mixer for complete exfoliation. The exfoliation of the clay may also be affected by use of high-shear mixers, (such as CB Loedige mixers, Schugi mixers, Littleford mixers, Drais mixers). The tip speed of any such mixers may for example be from at least 20 ms$^{-1}$, or at least 30 ms$^{-1}$ to for example 45 or 40 or 35 ms$^{-1}$.

In particular for water-swelling clays, the clay concentration may be kept low, for example below 20% by weight of the dispersion, or less than 10% or less than 5%, but typically at least 0.5% or at least 1% by weight, or order to obtain an exfoliated dispersion.

Commercially available clays comprising a dispersant may be used herein to form an exfoliated clay dispersion in a carrier liquid, e.g. aqueous carrier liquid, including water.

The clay dispersion may thus comprise at the most very small amounts of aggregated clay, but or (substantially) no aggregated clay particles, so it may be substantially free of aggregated clay. The dispersion may be filtered in order to remove aggregates. When the clay is completely exfoliated, the clay particles are present as individual clay particles, or typically platelets.

The amount of clay present in the second clay-crosslinked superabsorbent polymers, and hence in the coating herein, may be chosen depending on the stretchability required, and/or polymers chosen, and/or hydrophilicity required. Because said second clay-crosslinked superabsorbent polymers are only present as (and used to form) a coating, higher amounts of clay are economically feasible, for example from 10%, or from 20% or from 30% or from 40% to 90% or to 70% or to 50% by weight.

The liquid for said clay dispersion is water or a mixture of water and an organic liquid. Suitable liquids include at least 80% by weight water, at least 90% or even 100% by weight water.

Examples of suitable clays herein include (water swelling) smectite, (water swelling) mica, (water swelling) hectorite, including (water swelling) laponite (synthetic laponite), (water swelling) montmorillonite, (water swelling) saponite or (water swelling) synthetic mica containing sodium as interlayer ions, kaolin, or mixtures thereof; in one embodiment, montmorillonite, hectorite, including laponite or combinations thereof.

In embodiment herein, said exfoliation of said clay is obtained in said coating (spraying) step, e.g. by use of a high shear force spray tool, e.g. nozzle(s) as are known in the art, and further described herein. Then, even a non-exfoliated clay dispersion, or a partially exfoliated clay dispersion is introduced in said spraying step, and the clay is further or completely exfoliated therein by said nozzle.

The polymerisation reaction may comprise minor amounts of organic compounds that can provide covalent crosslinking between the polymers (so called organic covalent crosslinking agents), as known in the art, in addition to the cross-linking provided by said clay particles. Such small levels are for example less than 0.08% by weight of the polymerizable compounds, less than 0.05% by weight. In one embodiment however, it is highly that no such organic covalent crosslinking agents are present during the polymerization reaction, and that the second clay-crosslinked cross-linked superabsorbent polymers are free of covalent organic cross-linking agents and covalent organic cross-links.

Polymerization Process and Coating Process

The polymerization reaction may be done by providing a homogeneous mixture of said polymerizable compounds and said nano-sized clay particles, and typically said polymerization initiators, and optionally a polymerization catalyst.

Such a mixture may be a solution/dispersion of said polymerizable compounds in a liquid and a dispersion said nano-size clay particles in said liquid. In one embodiment, the polymerizable compounds are dissolved in a liquid, for example an aqueous liquid or even water, and said nano-size clay particles are dispersed therein, e.g. homogeneously dispersed therein and/or exfoliated clay dispersion, in any order. Alternatively, a solution of said polymerizable compounds in a liquid is obtained and separately, a dispersion of said clay in a liquid is obtained, and said two are combined, e.g. mixed to form the dispersion/solution as referred to herein, for example in step b) below. In the latter case, the liquids used are the same, e.g. aqueous liquids, or for example water.

The superabsorbent material herein is obtainable by a process comprising the steps of a) providing particles of said first superabsorbent polymers;

b) providing a solution/dispersion of said polymerizable compounds, and of said clay particles (e.g. the polymerizable compounds may for example be dissolved and the clay particles dispersed), and typically said dispersion/solution comprising a polymerization initiator;

c) applying said dispersion/solution of step c) on said particles of step a), thereby i) polymerizing said compounds, to form polymers, and crosslinking said polymers with said clay particles, and optionally further steps, to form said second clay-crosslinked superabsorbent polymers, and ii) forming a coating of said compounds and said clay, and/or resulting polymers on said particles of a); and d) drying the resulting particles of step c), to obtain said coated superabsorbent particles;

e) optionally, post-treating of the resulting particles of step d), such an annealing step, done subsequently to or simultaneously with step d).

The polymerization reaction and coating step may be conducted simultaneously, so that the polymerization, and clay-crosslinking, takes place during coating and possibly even after coating. Step b) above may thus be done only just before step c), so that the polymerization takes place mainly during coating step c).

The dispersion/solution of step b) is for example by forming a uniform dispersion of said clay particles in either water or a mixture of water and an organic solvent; and forming a solution of said polymerizable compounds in water and typically subsequently adding a polymerization initiator, combining said two, and then adding a polymerization initiator (and optionally a catalyst and/or optionally a organic cross linking agent). Thus, the separate solutions/dispersions are combined and then sued in step b).

Step b) may be done by first preparing a solution of said polymerizable compounds, and then adding said clay to obtain a (homogeneous) dispersion of (exfoliated) clay in said compound solution in a liquid, e.g. water, and then typically adding a polymerization initiator and optionally catalyst.

Alternatively, there is a single solution/dispersion formed of said compounds and clay (and used) in step b), to which then typically a polymerization initiator is added, (just) prior to the coating step c) takes place.

This dispersion/solution(s), or combination thereof, obtained in step b) are typically used immediately in step c) to form the coating, so that the polymerization of said compounds and crosslinking by said clay particles takes place on the surface of said first superabsorbent polymer particles, to form a coating of said second clay-crosslinked superabsorbent polymers, crosslinked by said clay particles. The latter may be a gel-like material, forming a gel-like coating (containing water, which may then be dried to obtain a less gel-like, e.g. solid and/or amorphous coating).

Alternatively, the polymerization and clay-crosslinking may take place in said dispersion/solution first and the resulting second clay-cross-linked superabsorbent polymers are then applied to said first superabsorbent polymers as a coating/coating layer. This may then be followed by an annealing step, to form a more coherent coating.

The concentration of the polymerizable compound, e.g. monomers in said liquid, e.g. in said aqueous liquid/solution, may be varied over a wide range. Generally, it is at least 25% by weight, at least 35% by weight, up to a saturation concentration.

The resulted coated first superabsorbent polymer (particles) are typically dried, e.g. to remove said liquid used to make the dispersion/solution. Any gel-like coating may then become less gel-like; e.g. a solid, optionally amorphous, coating.

By drying the second clay-crosslinked superabsorbent polymers and by reducing the water content to, e.g. to less than 5%, or less than 1% by weight of said second clay-crosslinked polymers, or of said coated superabsorbent polymer particles, the convertibility of the superabsorbent material is improved, and the risk of tackiness is reduced.

The polymerization temperature should be selected in accordance with the selected polymerizable compounds (e.g. and said the polymerization initiator); this is typically within a range from 0° C. to 200° C., or from 20° C. to 100° C.

The dispersion/solution may be applied to the first superabsorbent polymer particles by any method, for example by spraying. This may be done by any spraying method, for example using a fluidized bed.

The application of the coating may be done in a (spray) tower or fluidized bed reactor (herein referred to as fluidized bed). Hereby, the particles and fluidized in a gas stream and first superabsorbent polymers and the dispersion/solution(s) is/are introduced into the fluidized bed's gas stream, so that the dispersion/solution(s) coat the surface of said first polymers (e.g. particles), as known in the art. Said introduction of said solution/dispersion is done by spraying said solution/dispersion into said fluidized bed (e.g. into said gas stream).

It should be noted that the nano-size clay dispersion may be applied (sprayed) separately from the polymerizable compound solution/dispersion, forming only said mixture once applied to said first polymers.

The spraying conditions (such as speed, temperature and amounts) are typically chosen such that the resulting coating is thin and homogeneous, e.g. having a weight average coating caliper of for example from 1 or 2 to 20 μm, 1 or 2 to 10 μm, applicable over the coating as a whole, as described above.

If the polymerizable compound has precursor groups, e.g. anionic group precursors, such as an amide or ester group, the resulting coating of said clay-crosslinked polymers may be partially or completely hydrolyzed, to obtain the coating of said second clay-crosslinked superabsorbent polymers, e.g. polyelectrolytes, e.g. anionic polyelectrolytes, such as polyacrylates.

For said coating, it is not essential that said hydrolysis is complete. Whilst the absorbent capacity of fully hydrolyzed polyelectrolytes (such as polyacrylates—so fully hydrolyzed esters/amides thereof) is higher, this property is not too important for the coating. Hence, a fast but partial hydrolysis is possible, and may be used herein for process or cost reasons.

The hydrolysis may be done by applying, e.g. spraying, a basic solution on the surface of the coated particles. This may for example be done in the same spray tower or fluidized bed. For example, an aqueous solution of NaOH may be used, for example of a concentration of 0.01%-20% by weight, preferably 0.1-1% by weight, or an aqueous solution of sodium carbonate (0.01-20%, preferably 0.1-5% by weight).

Said basic solution, e.g. NaOH or $Na_2CO3$ solution, may comprise alcohol (e.g. ethanol or isopropanol) to further control the penetration depth of the hydrolysis solution in said coating. The alcohol:water ratio may be from 9:1 to 1:9, or from 8:1 to 1:3, or from 5; 1 or from 3:1 or 2:1, to 1:3, or to 1:2, or for example about 1:1 alcohol/water mixture.

Furthermore, it is believed that the presence of alcohol also enhances the reactivity of the basic hydrolysis solution and enhances the reaction speed; Na-ethanolate is formed, which is more nucleophilic and hence more reactive in the nucleophilic substitution reaction underlying hydrolysis.

The hydrolysis may for example be done at a temperature of for example 40° to 95° C., preferably 50-80° C. This may be a higher temperature than employed during the coating and/or polymerization step. The hydrolysis may be done for any length of time, until desired degree of conversion is reached. The conversion can be determined by IP spectroscopy.

The resulting particles may be further treated, such as by an optional purification step, to remove by-product of hydrolysis (alcohol). However, this purification may be done simultaneously with the drying step. For example, the precursor groups herein are for example ethyl ester groups or methyl ester groups, and then, the reaction product of the hydrolysis is ethanol or methanol, which is volatile and removed during the drying step An alternative hydrolysis route may be to suspend the coated particles in for example an alcohol or an alcohol/water mixture, as above; hereby, the alcohol content may be chosen to be higher, e.g. 50-100%, preferably 90-100%, whereto then the basic compounds, such as NaOH is added.

Then, the coated particles are dried to remove the fluid, e.g. water, and optional alcohol, for example in said tower or fluidized bed, or in a separate drying equipment, such as a separate drying tower or fluidized bed, for example at a temperature of at least 40° C., or at least 60° C., up to for example 200° C., or to 150° C.

Alternatively, as mentioned above, the step b) and polymerization and clay-crosslinking, and optionally said subsequent hydrolysis of polymers comprising precursors, is done first, to form said second clay-crosslinked superabsorbent polymers, in the form of a dispersion or in the form of a latex in a fluid, e.g. aqueous fluid, or even water.

This dispersion or latex is then applied in step c), for example sprayed, onto said first superabsorbent polymer particles. Any of the process steps and conditions above may then apply.

Said process may, in particular in said latter case, comprises a step to form a homogeneous and/or coherent coating of said second clay-crosslinked superabsorbent polymers, for example an annealing step at a temperature of for example 60-200° C. Annealing may be done during drying, or it may be an additional step. It may for example be done in a tower or fluidized bed, e.g. the same tower or fluidized bed as the coating step.

Suitable "spraying" process steps for spraying a dispersion/solution into a gas phase, such as in a tower of fluidized bed, are for example described in EP-A-0 348 180, WO-A-96/40427, and U.S. Pat. No. 5,269,980.

The particles are preferably transferred in the gas-fluidized state from the step c) (coating and/or polymerization) into at least the drying process steps d). Particularly preferred may be that all process steps of coating, polymerization of the coating, optionally hydrolysis, drying and optionally further steps, such as annealing, are in fluidized state.

Preferred is that in a fluidized bed used herein a suitable carrier gas flows upwardly so that the particles form a fluidized layer.

The carrier gas is may (preferably) be an inert gas; this may for example be nitrogen. The gas velocity is preferably such that the flow, e.g. in the tower or fluidized bed, is for example from 0.01 to 2.5 m/s and preferably in the range from 0.1 to 1.0 m/s. The carrier gas is advantageously preheated to the reaction temperature upstream of the reactor.

Alternatively the homogeneous nano-size clay dispersion is obtained in situ, by use of a high shear spray nozzle used in the spraying step. Then, a dispersion of clay particles and a liquid are introduced in a spray nozzle, and said nozzle exfoliates the clay and ensures the formation of a homogeneous dispersion of said exfoliated clay. Such high shear spray nozzles are known in the art of "microfluidizer" techniques, used for exfoliation.

This dispersion is then used to form a coating, as described above.

The coating spraying step herein may use a spraying tool to spray a spray-stream of the (combined) clay dispersion(s) and polymerizable compound dispersion or solution(s), and typically an initiator, into a vessel comprising said first superabsorbent polymer material, typically in fluidized state. The spray tool has an inlet for the combined dispersion/solution of the clay and polymerizable compound, or multiple inlets for different dispersion(s)/solution(s), that are then combined prior to leaving said spray tool trough an outlet. The tool has typically multiple outlets, to provide multiple spray-streams, that will contact the first superabsorbent polymers to form a coating.

Said inlet or multitude of inlets thus typically lead, respectively, from a reservoir with a dispersion/solution as described above, or multitude of such reservoirs, to said outlet(s) of the spray tool; hereby said outlet(s) form the dispersion/solution, or now combined dispersions/solutions into a spray-stream or a multitude of spray-streams (or in one embodiment herein into droplets). Said reservoir(s) may possibly be cooled and/or shielded from radiation. The reservoir may have a pump and said inlet(s) may have a valve(s) for controlling the flow of the dispersion(s)/solution(s). In addition, or alternatively, pressure may be applied to said spray tool via another pressure source to force the dispersion(s)/solution(s) through the spray tool.

The inlet(s) may comprise a tool for mixing the clay dispersion, polymerizable (monomer) compound dispersion/solution, and/or initiator, or combination thereof. The spray tool may be temperature controlled.

Because the polymerization of the polymerizable compounds (monomers) may begin almost instantaneously upon the mixing of the initiator, the temperature of inlet may be reduced by cooling, e.g. to the temperatures specified herein. Cooling of the reservoirs, inlets etc. may be done by any means, for example be done by water bath, refrigeration coils, insulation. Said vessel may comprise a gaseous atmosphere, e.g. a controlled and heated gaseous atmosphere. It may be a substantially inert atmosphere, such as nitrogen gas, that may comprise small levels of oxygen, for example less than 5% by weight or less than 3% by weight or less than 1% by weight.

Suitable spray tools are known in the art and for example described in U.S. Pat. No. 5,269,980 and US2008/242817 and WO96/40427. So-called aerosol generators, incorporating provisions for droplet formation and droplet size control, as known in the art, capable of producing a spray-stream comprising, or in the form of, spherical and/or monodisperse droplets of the dispersion/solution(s) herein.

The coating may be applied by use of a spray tool having an orifice plate with a plurality of orifices, or it may have a plurality of nozzles with each orifices, with a suitable diameter chosen to the required size of the spray-stream or droplets thereof.

The number of outlets, e.g. orifices, may be for example at least 5, or at least 10, more at least 50 and typically up to 1000 or up to 500. The diameter of the outlets, e.g. orifices, may be at least 50 µm, or at least 75 µm and more, at least 100 µm and typically up to 1000 µm, up to 800 µm and more up to 600 µm.

During the time in said vessel, the carrier liquid (s) may be (continuously) dried-off and evacuated from the atmosphere, to that the resulting coated superabsorbent polymers, with said second clay-crosslinked superabsorbent polymer coating, have a liquid content (including water) of less than 10% by weight, or as defined herein above.

The atmosphere in reaction chamber is heated to a temperature of from about 50° C. or 60° C. or 70° C., to 250° C., to 200° C. or to 150° C. The relative humidity of the gas in the vessel may be low, in order to speed up drying, e.g. being below 30%.

The spraying with the solution/dispersion may also, for example, be carried out in mixers such as screw mixers, paddle mixers, disk mixers, plowshare mixers and shovel mixers. Useful mixers include for example Lödige® mixers, and Schugi® mixers.

Absorbent Structures

The absorbent structure of the invention may be any absorbent structure, used to absorb and retain liquids, such as urine or blood.

The absorbent structure is typically, or forms typically part of, a disposable absorbent article, such as interlabial products, sanitary napkins or panty liners; or adult incontinence products, such as pads or diapers; or baby, infant or toddler diapers, including training pants.

If the absorbent structure is part of a disposable absorbent article, then the absorbent structure of the invention is typically that part of an absorbent article which serves to store the bodily fluid, e.g. the storage layer of an absorbent article, also referred to as absorbent core. As known in the art, this may be in direct contact with an acquisition layer, or in one embodiment of the invention, it may form a unitary structure with an acquisition layer In yet another embodiment of the invention the absorbent structure is an acquisition layer for use in an absorbent article.

The absorbent structure may be a structure that consists of the superabsorbent material and that is then shaped into the required structure, or, it may comprise additional components, such as those used in the art for absorbent structures. The absorbent structure may comprise the superabsorbent material herein at any weight level or concentration. For example, the absorbent structure may also comprise one or more support or wrapping materials, such as foams, films, woven webs and/or nonwoven webs. In particular when the absorbent structure is a storage layer of an absorbent article above, or when the absorbent structure comprises a layer that serves as storage layer, the structure or layer comprises large amounts of the superabsorbent material herein, compared to possible other components of the structure; the superabsorbent material is present at a level of more than 50% by weight of the structure, or even more than 70% by weight, or even more than 80% by weight, or even more than 90% by weight of the structure. The absorbent structure herein may comprise a structuring agent or matrix agent, such as non-absorbent fibers, and/or a thermoplastic component, such as a thermoplastic adhesive, or for example a non-absorbing fibrous thermoplastic adhesive component. The absorbent structure may comprise, alternatively or in addition, absorbent fibrous material, such as an airfelt material cellulose fibers etc., which can provide a matrix for immobilization of the superabsorbent material.

However, if the absorbent structure is a liquid storage layer or when the absorbent structure comprises one or more liquid storage layers, said liquid structure or said liquid storage layer comprises large amounts of the superabsorbent material herein and only very little or no absorbent (cellulose) fibers, e.g. less than 40% weight of the structure, or less than 20% by weight or less than 10% by or less than 5% by weight (of said structure) of said absorbent fibrous (cellulose) material; and/or more than 50% or more than 70% or more than 80% or more than 90% by weight (of the structure) of the superabsorbent material herein. The weight ratio of the superabsorbent material to any optional absorbent or non-absorbent fibers, or other matrix agents, is at least 1:1, at least 3:2 or at least 2:1, or at least 3:1 or at least 4:1.

The absorbent structure comprises at least a wrapping material, which wraps (the portion comprising) the superabsorbent material, a so-called core wrap material. In one embodiment, the core wrap material comprises a top layer and a bottom layer, the latter being furthest away from the skin of the user, whereby the core wrap material as a whole or the top layer and/or the bottom layer can be provided from for example a nonwoven material, such as spunbond, melt-blown and/or carded nonwovens. One material is a so-called SMS material, comprising a spunbonded, a melt-blown and a further spunbonded layer. Permanently hydrophilic non-wovens, and in particular nonwovens with durably hydrophilic coatings are suitable herein. An alternative material comprises a SMMS-structure. The top layer and the bottom layer may be provided from two or more separate sheets of materials or they may be alternatively provided from a unitary sheet of material Non-woven materials are provided from synthetic fibers, such as PE, PET and PP. As the polymers used for nonwoven production are inherently hydrophobic, they are coated with hydrophilic coatings, e.g. coated with nanoparticles, as known in the art.

In an embodiment of the present invention the absorbent structure comprises: a wrapping material, the superabsorbent material described herein, and a thermoplastic material and/or an adhesive and/or a thermoplastic adhesive, which may be in the form of non-absorbing fibers.

Absorbent structures can for example be made as follows:
a) providing a substrate material that can serve as a wrapping material;
b) depositing the superabsorbent material herein onto a first surface of the substrate material, (for example in a pattern comprising at least one zone which is substantially free of superabsorbent material, and the pattern comprising at least one zone comprising superabsorbent material, such that openings are formed between the separate zones with the superabsorbent material);
c) depositing a thermoplastic and/or adhesive material onto the first surface of the substrate material and the superabsorbent material, such that part of the thermoplastic/adhesive material is in direct contact with the first surface of the substrate and part of the thermoplastic/adhesive material is in direct contact with the superabsorbent material;
d) and then typically closing the above by folding the substrate material over, or by placing another substrate material over the above.

Disposable absorbent article comprising the absorbent structure of the invention are sanitary napkins, panty liners, adult incontinence products and baby or toddler or so-called infant diapers, including training pants, whereby articles which serve to absorb urine, e.g. adult incontinence products (pads and diapers), and (baby, infant, toddler) diapers, including training pants are the most articles herein.

Articles herein may have a topsheet and a backsheet, which each have a front region, back region and crotch region, positioned therein between. The absorbent structure of the invention is typically positioned in between the topsheet and backsheet. Backsheets are vapour pervious but liquid impervious. Topsheet materials are at least partially hydrophilic; are also so-called apertured topsheets.

These absorbent articles typically comprise a liquid impervious (air or water vapour pervious) backsheet, a fluid pervious topsheet joined to, or otherwise associated with the backsheet. Such articles are well known in the art and fully disclosed in various documents mentioned throughout the description.

Because the superabsorbent material herein has a very high absorbency capacity, it is possible to use only low levels of this material in the absorbent articles herein. Thus thin absorbent articles, such as adult and infant diapers, training pants, sanitary napkins comprising an absorbent structure of the invention, the articles having an average caliper (thickness) in the crotch region of less than 1.0 cm, less than 0.7 cm, more less than 0.5 cm, or even less than 0.3 cm (for this purpose alone, the crotch region being defined as the central zone of the product, when laid out flat and stretched, having a dimension of 20% of the length of the article and 50% of the width of the article).

A diaper herein has a front waist band and a back waist band, whereby the front waist band and back waist band each have a first end portion and a second end portion and a middle portion located between the end portions, and whereby the end portions comprise each a fastening system, to fasten the front waist band to the rear waist band or whereby the end portions are connected to one another, and whereby the middle portion of the back waist band and/or the back region of the backsheet and/or the crotch region of the backsheet comprises a landing member, the landing member comprising second engaging elements selected from loops, hooks, slots, slits, buttons, magnets. Most are hooks, adhesive or cohesive second engaging elements. The engaging elements on the article, or diaper are provided with a means to ensure they are only engage able at certain moments, for example, they may be covered by a removable tab, which is removed when the engaging elements are to be engaged and may be re-closed when engagement is no longer needed, as described above.

Diapers and training pants herein have one or more sets of leg elastics and/or barrier leg cuffs, as known in the art.

Methods:

The measurements should be carried out, unless otherwise stated, at an ambient temperature of 23±2° C. and a relative humidity of 50±10%.

Water Content

The water content s referred to herein is measured by the EDANA method referred to above.

Centrifuge Retention Capacity (CRC)

Centrifuge Retention Capacity as referred to herein is determined by EDANA (European Disposables and Nonwovens Association) recommended test method No. 441.2-02 "Centrifuge retention capacity".

Extractables

The extractable fractions of the water-absorbing polymeric particles are determined in accordance with EDANA (European Disposables and Nonwovens Association) recommended test method No. 470.2-02 "Extractables".

EDANA test methods are obtainable for example at European Disposables and Nonwovens Association, Avenue Eugene Plasky 157, B-1030 Brussels, Belgium.

Determination of the Coating Caliper and Coating Caliper Uniformity

The coatings on said first superabsorbent polymers (particles) herein can typically be investigated by standard scanning electron microscopy, environmental scanning electron micrsocopy (ESEM) as known to those skilled in the art. In the following method the ESEM evaluation is also used to determine the average coating caliper and the coating caliper uniformity of the coated superabsorbent polymers/materials via cross-section of the materials.

Equipment model: ESEM XL 30 FEG (Field Emission Gun)

ESEM setting: high vacuum mode with gold covered samples to obtain also images at low magnification (35×) and ESEM dry mode with LFD and bullet without PLA (Pressure Limiting Aperture) to obtain images of the coating (layer) as they are (no gold coverage required).

Filament Tension: 3 KV in high vacuum mode and 12 KV in ESEM dry mode.

Pressure in Chamber on the ESEM dry mode: from 0.3 Torr to 1 Torr on gelatinous samples and from 0.8 to 1 Torr for other samples.

Samples of said coated first superabsorbent polymer particles or (of uncoated first superabsorbent polymers particles) can be observed after about 1 hour at ambient conditions (20 C, 80% relative humidity) using the standard ESEM conditions/equipment.

Then, the same samples can be observed in high vacuum mode. Then the samples can be cut via a cross-sectional cut with a teflon blade (Teflon blades are available from the AGAR scientific catalogue (ASSING) with reference code T5332), and observed again under vacuum mode.

The coatings have different morphology than the first superabsorbent polymer particle and the coating (layer) are clearly visible in the ESEM images, in particular when observing the cross-sectional views.

The average coating caliper is determined then by analyzing at least 5 particles of the coated first superabsorbent polymers herein and determining 5 average calipers, an average per particle (by analyzing the cross-section of each particle and measuring the caliper of the coating in at least 3 different areas) and taking then the average of these 5 average calipers.

The uniformity of the coating is determined by determining the minimum and maximum caliper of the coating (layer) via ESEM of the cross-sectional cuts of at least 5 different particles and determining the average (over 5) minimum and average maximum caliper and the ratio thereof.

If the coating is not clearly visible in ESEM, then staining techniques known to the skilled in the art that are specific for the coating applied may be used, such as enhancing the contrast with osmium tetraoxide, potassium permanganate and the like, e.g. prior to using the ESEM method.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention

What is claimed is:

1. A superabsorbent material, comprising: first superabsorbent polymers, coated with second clay-crosslinked superabsorbent polymers, said second clay-crosslinked superabsorbent polymers being polymerized in a solution or dispersion of polymerizable compounds, in the presence of a clay particle dispersion, crosslinked by said clay particles, said clay particles having a weight average largest particle dimension of less than 800 nm; said coating of said second clay-crosslinked superabsorbent polymers having an average caliper from 1 micron to 100 microns.

2. The Superabsorbent material of claim 1, wherein said coated first superabsorbent material is in the form of particles having a core of said first superabsorbent polymers, coated with said second clay-crosslinked superabsorbent polymers.

3. The Superabsorbent material of claim 1, wherein said polymerizable compounds have a charged group and/or precursor thereof, and said resulting second polymers have a charged group and/or precursor thereof.

4. The Superabsorbent material of claim 1, wherein said first superabsorbent polymers are free of clay particles of a weight average largest particle dimension of less than 800 nm.

5. The Superabsorbent material of claim 1, wherein, said first superabsorbent polymers are anionic polyelectrolyte polymers.

6. The Superabsorbent material of claim 1, wherein said first polymers are cross-linked via organic cross-linkers.

7. The Superabsorbent material of claim 1, wherein said second clay-crosslinked superabsorbent polymers include anionic polycarboxylate polymers, obtainable by polymerization of ester and/or amide group-containing monomers in the presence of said clay particles, to form polyester and/or polyamide polymers that are crosslinked by said clay particles, and subsequent hydrolysis of said polyester and/or polyamide polymers to obtain said second clay-crosslinked superabsorbent polymers, including anionic polycarboxylate polymers.

8. The Superabsorbent material of claim 1, wherein said clay is selected from the group consisting of montmorillonite, laponite, saponite and hectorite, and combinations thereof.

9. The Superabsorbent material of claim 1, wherein said dispersion of clay particles is a homogeneous dispersion of exfoliated clay particles that are platelets.

10. The superabsorbent material of claim 1, wherein said coating of said second clay-crosslinked superabsorbent polymers has an average caliper from 2 microns to 20 microns.

11. A superabsorbent material, comprising: first superabsorbent polymers, coated with second clay-crosslinked superabsorbent polymers, said second clay-crosslinked superabsorbent polymers being polymerized in a solution or dispersion of polymerizable compounds, in the presence of a clay particle dispersion, crosslinked by said clay particles, said clay particles having a weight average largest particle dimension of less than 800 nm; said coating of said second clay-crosslinked superabsorbent polymers having a ratio of the smallest to the largest caliper from 1:1 to 1:5.

12. The superabsorbent material of claim 11, wherein said coated first superabsorbent material is in the form of particles having a core of said first superabsorbent polymers, coated with said second clay-crosslinked superabsorbent polymers.

13. The superabsorbent material of claim 11, wherein said polymerizable compounds have a charged group and/or precursor thereof, and said resulting second polymers have a charged group and/or precursor thereof.

14. The superabsorbent material of claim 11, wherein said first superabsorbent polymers are free of clay particles of a weight average largest particle dimension of less than 800 nm.

15. The Superabsorbent material of claim 11, wherein, said first superabsorbent polymers are anionic polyelectrolyte polymers.

16. The superabsorbent material of claim 11, wherein said first polymers are cross-linked via organic cross-linkers.

17. The superabsorbent material of claim 11, wherein said second clay-crosslinked superabsorbent polymers include anionic polycarboxylate polymers, obtainable by polymerization of ester and/or amide group-containing monomers in the presence of said clay particles, to form polyester and/or polyamide polymers that are crosslinked by said clay particles, and subsequent hydrolysis of said polyester and/or polyamide polymers to obtain said second clay-crosslinked superabsorbent polymers, including anionic polycarboxylate polymers.

18. The superabsorbent material of claim 11, wherein said clay is selected from the group consisting of montmorillonite, laponite, saponite and hectorite, and combinations thereof.

19. The superabsorbent material of claim 11, wherein said dispersion of clay particles is a homogeneous dispersion of exfoliated clay particles that are platelets.

20. The superabsorbent material of claim 11, wherein said coating of said second clay-crosslinked superabsorbent polymers has an average caliper from 1 micron to 100 microns.

* * * * *